United States Patent [19]
Martin et al.

[11] Patent Number: 5,848,895
[45] Date of Patent: Dec. 15, 1998

[54] SLEEVE FOR DENTAL INSTRUMENT NOZZLE

[76] Inventors: Daniel H. Martin; Todd E. Davis, both of 757 SE. 17th St. #383, Fort Lauderdale, Fla. 89123

[21] Appl. No.: 935,031

[22] Filed: Sep. 22, 1997

[51] Int. Cl.[6] ..................................................... A61C 1/16
[52] U.S. Cl. ........................... 433/116; 206/364; 206/368
[58] Field of Search ....................... 206/275, 306, 206/363, 438, 368, 63.5, 439, 771, 364, 369, 571; 433/116; 600/186; 229/87.05; 383/209; 604/171, 172

[56] References Cited

U.S. PATENT DOCUMENTS

| | | |
|---|---|---|
| 2,121,373 | 6/1938 | Turner . |
| 3,050,066 | 8/1962 | Koehn ........................................ 604/97 |
| 3,189,227 | 6/1965 | Hobbs et al. . |
| 3,473,646 | 10/1969 | Burke ....................................... 206/571 |
| 3,513,830 | 5/1970 | Kalayjian ................................. 206/363 |
| 3,648,704 | 3/1972 | Jackson ..................................... 604/172 |
| 5,048,684 | 9/1991 | Scott ......................................... 206/364 |
| 5,217,370 | 6/1993 | Craig et al. .............................. 433/116 |
| 5,460,619 | 10/1995 | Esrock ....................................... 433/80 |
| 5,480,302 | 1/1996 | Fife ........................................... 433/116 |

*Primary Examiner*—Cary E. O'Connor

[57] ABSTRACT

A sleeve for disposable dental instrument nozzles is disclosed. The sleeve is designed to maintain sterility from the point of manufacture until actual use with a patient. Both ends of the sleeve are designed to be easily punctured or removed.

10 Claims, 1 Drawing Sheet

SLEEVE FOR DENTAL INSTRUMENT NOZZLE

BACKGROUND OF THE INVENTION

1. Field of the Invention

In common use in the dental profession are various handheld instruments which either deliver media flows to the mouth, or are used to vacuum excess saliva and debris. One example is the three way syringe, used for discharging pressurized air and water flows into the mouth. The syringe is commonly covered with a plastic sleeve to prevent exterior contamination from bacteria, viruses, and other pathogenic substances. Syringes typically include a discharge nozzle which is detachable because of the necessity to sterilize or replace it before use with a new patient. Commonly, the nozzle is replaced after each use, because of the expense and difficulty of sterilization.

The present invention relates to the cleanliness of the nozzle. Although the dental practitioner commonly replaces the nozzle between patients, very often the single use nozzles are stored in a bulk container. When removing a nozzle for use, it is possible that the practitioner's hands might remain contaminated from the previous patient, and the remaining nozzles would therefore become contaminated. Some pathogens are airborne and could contaminate the nozzles despite the practitioner's sanitation efforts. In the event that the nozzle escaped contamination while stored in bulk, it is still possible that a sneeze or other airborne contaminant might infect it after it is inserted into the syringe, but before it is used with the patient. Typically, the practitioner will replace the nozzle as soon as treatment with a patient is complete, and it is possible for an unused nozzle to be left in the syringe for many minutes, or even overnight, before being used with the next patient.

2. Description of the Prior Art

U.S. Pat. No. 4,810,194 seeks to provide an antiseptic shield for the dental syringe, but does not attempt to cover the discharge nozzle.

As evidenced on page 299 of the Darby Dental Supply Co., Inc. Fall/Winter 1996 catalog, disposable nozzles are commonly packaged in quantities ranging from 150 to 1,600 nozzles in one bag. Generally, the practitioner uses one nozzle per patient. The dental assistant may use one additional nozzle per patient. Therefore, the nozzles risk contamination from the moment the dental practitioner or assistant opens the bag, until the completion of 75 to 1600 patient treatments.

SUMMARY OF THE INVENTION

The present invention provides for an elongate disposable dental syringe discharge nozzle sanitary sleeve. The sleeve is constructed of a material which prevents penetration of bacteria, viruses, and other pathogens; and is designed to provide sterility from the point of manufacture until actual usage with a patient.

Both ends of the sleeve are designed to be easily punctured or removed. This allows the end of the sleeve nearest the proximal end of the nozzle to be easily punctured or removed, so that the nozzle can be inserted into the dental syringe while still covered. This prevents the nozzle from being contaminated until actual use with the patient. For ease of manufacturing, both ends of the sleeve are designed the same so that the nozzle does not require orienting before inserting it into the sleeve.

BRIEF DESCRIPTION OF THE DRAWINGS

Advantageous modifications and features of the invention can now be readily ascertained from the following detailed description thereof, taken in conjunction with the accompanying drawings; in which.

DETAILED DESCRIPTION

Figure 1:
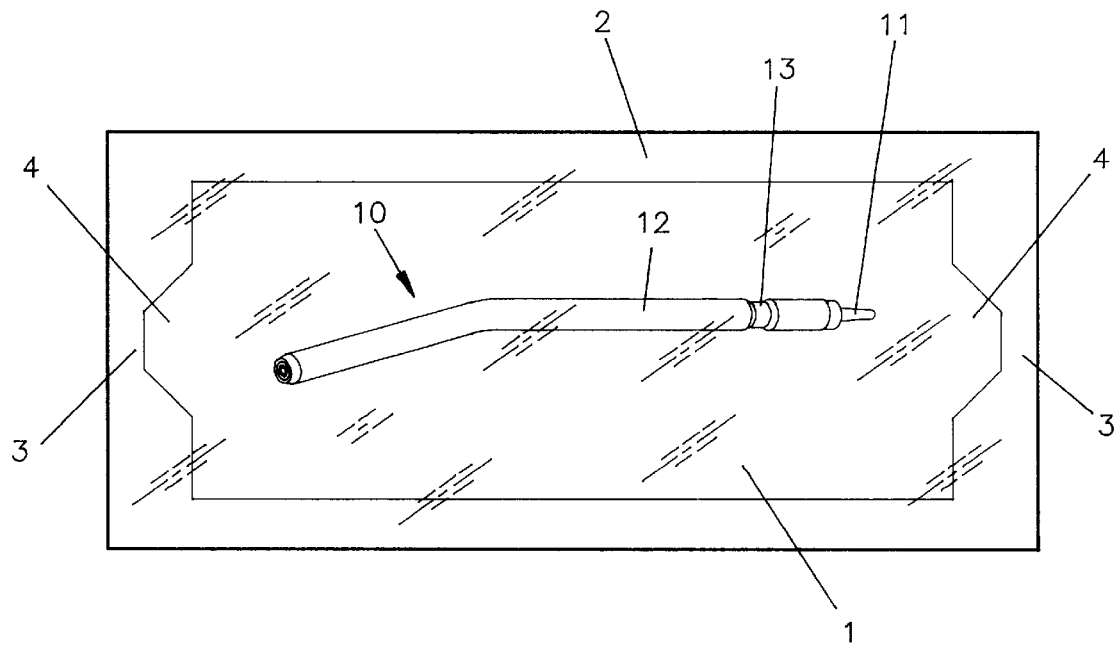
FIG. 1 is a perspective view of a dental discharge nozzle enclosed within the inventive sleeve incorporating a narrowing of the seal.

The illustrated dental syringe discharge nozzle 10 consists of an inner tube 11, an outer tube 12, and a retention groove 13.

The dental nozzle sleeve is constructed of one or more sheets 1 made of plastic or other material which will prevent penetration of bacteria, viruses, and other contaminants. A seal 2 is created by use of a heat weld, adhesive, or other sealing mechanism of such nature as to maintain the sterility of the enclosed nozzle 10.

In the embodiment shown in FIG. 1, both ends of the sleeve are constructed with a narrow portion 3 of the seal 2. When the dental practitioner prepares to insert the nozzle 10 into a dental syringe, the proximal end of the nozzle 10 can be easily guided into the V-shaped recess 4 of the seal 2, and then punctured through the narrow portion 3 of the seal 2. The conscientious practitioner can push the nozzle out just past the retention groove 13, so that the portion of the nozzle which is not covered by the dental instrument remains covered by the sleeve.

Figure 2:
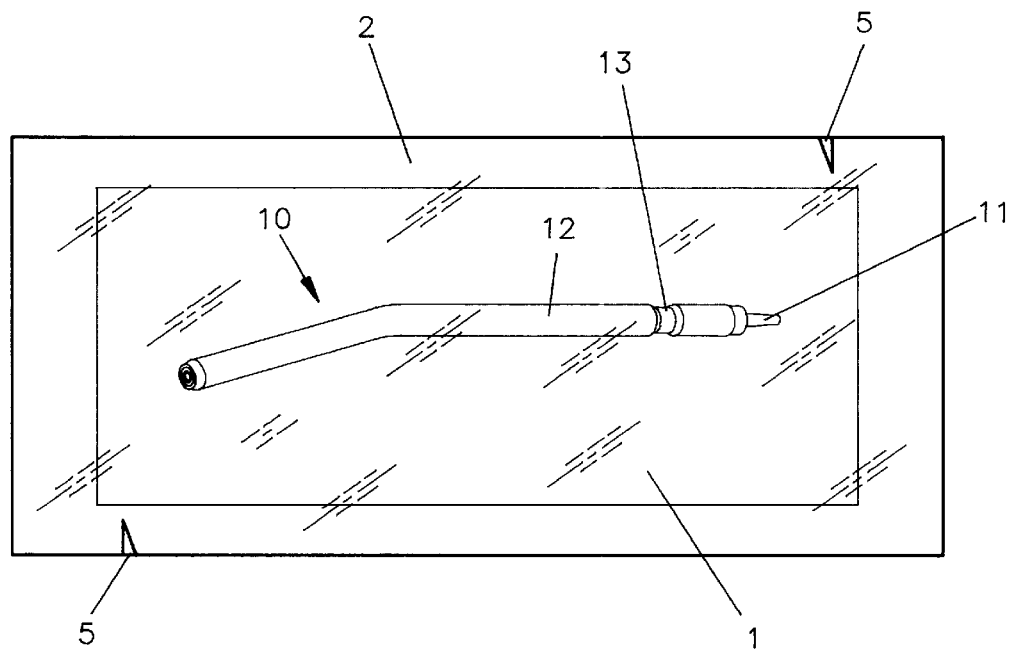
FIG. 2 is a perspective view of a dental discharge nozzle enclosed within the inventive sleeve incorporating a narrowing of the seal and a notched perforation of the edge seal.

In the embodiment shown in FIG. 2, both ends of the sleeve are constructed with a notched portion 5 of the seal 2. The proximal end of the sleeve can be easily torn from this notch when the practitioner prepares to insert the nozzle 10. The conscientious practitioner can use the remainder of the sleeve to hold the nozzle 10 while inserting it into the dental syringe, and then leave the sleeve in place until actual usage of the syringe.

References herein to the details of the illustrations are by way of example only and not intended to limit the scope of the claims which themselves recite those details regarded as important to the invention.

What is claimed is:

1. A dental instrument nozzle assembly comprising:
   a) a dental instrument nozzle comprising a proximal end for connection with a dental instrument; and
   b) an enclosure about said dental instrument nozzle comprising
      1) one or more sheets of flexible material,
      2) a hermetic seal about the periphery of the flexible material to prevent contamination, and
      3) at least one end of the enclosure constructed with a narrowed seal so that the proximal end of the nozzle can more easily puncture the end of the enclosure.

2. The enclosure of claim 1 wherein both ends of the enclosure are constructed with similar or identical features, so that the seal at each end is substantially equally puncturable.

3. A dental instrument nozzle assembly comprising:
   a) a dental instrument nozzle comprising a proximal end for connection with a dental instrument; and
   b) an enclosure about said dental instrument nozzle comprising
      1) one or more sheets of flexible material,
      2) a hermetic seal about the periphery of the flexible material to prevent contamination, and 3) the seal on at least one side of the enclosure constructed with a weakened portion near the end of the enclosure, so that the remaining portion of the seal and flexible material on that end of the enclosure can be easily severed from the remainder of the enclosure when opposite sides of the weakened portion are pulled apart.

4. The enclosure of claim 3 wherein both ends of the enclosure are constructed with similar or identical features, so that each end of the enclosure is substantially equally severable.

5. An infection control method for dental instrument nozzles comprising:

a) inserting a dental instrument nozzle into an enclosure;
   b) forming a hermetic seal about the periphery of the enclosure;
   c) setting the nozzle and enclosure aside until ready for use with a patient;
   d) puncturing the enclosure with one end of the nozzle.

6. The infection control method of claim 5 wherein the enclosure is punctured with the proximal end of the nozzle and further comprising:

e) connecting the proximal end of the nozzle to a dental instrument;
   f) removing the enclosure from the nozzle when ready to use the dental instrument with a patient.

7. The infection control method of claim 5, wherein the dental instrument nozzle is sterilized before it is inserted into the enclosure.

8. An infection control method for dental instrument nozzles comprising:

a) inserting a dental instrument nozzle into an enclosure;
   b) forming a hermetic seal about the periphery of the enclosure;
   c) setting the nozzle and enclosure aside until ready for use with a patient;
   d) removing the end of the enclosure when the nozzle is needed for use with a patient.

9. The infection control method of claim 8 wherein the end of the enclosure removed is the end nearest the proximal end of the nozzle and further comprising:

e) connecting the proximal end of the nozzle to a dental instrument;
   f) removing the enclosure from the nozzle when ready to use the dental instrument with a patient.

10. The infection control method of claim 8, wherein the dental instrument nozzle is sterilized before it is inserted into the enclosure.

* * * * *